United States Patent [19]

Boutos

[11] Patent Number: 5,704,894
[45] Date of Patent: Jan. 6, 1998

[54] PNEUMATIC APPARATUS FOR CONTROLLING CERTAIN BODILY INSERTION DEVICES AND COLLAPSIBLE SEATING APPARATUS

[76] Inventor: David Boutos, 4420 Dunlap Crossing St., Las Vegas, Nev. 89129

[21] Appl. No.: 648,492

[22] Filed: May 15, 1996

Related U.S. Application Data

[62] Division of Ser. No. 368,907, Jan. 5, 1995, Pat. No. 5,586,560.

[51] Int. Cl.⁶ ..................................................... A61F 5/00
[52] U.S. Cl. ................................................................ 600/38
[58] Field of Search .......................... 128/845, DIG. 20; 600/38–41; 602/13; 601/134, 135

[56] References Cited

U.S. PATENT DOCUMENTS

| | | | |
|---|---|---|---|
| 2,342,557 | 2/1944 | Ross | 601/134 |
| 2,657,687 | 11/1953 | Bonham | 601/135 |
| 2,685,287 | 8/1954 | Golfier | 601/135 |
| 3,228,392 | 1/1966 | Speyer | 601/134 |
| 3,831,592 | 8/1974 | Lancellotti | 601/135 |
| 4,002,164 | 1/1977 | Bradley | 601/135 |
| 4,722,327 | 2/1988 | Harvey | 600/41 |
| 5,076,261 | 12/1991 | Black | 601/93 |
| 5,460,597 | 10/1995 | Hopper | 601/134 |

*Primary Examiner*—Michael A. Brown
*Attorney, Agent, or Firm*—Meschkow & Gresham, P.L.C.

[57] ABSTRACT

A seating apparatus having a base, front and rear upright support members, and two vertical transverse support members. The transverse members comprise the seating means. Extending from the rear upright support members are two vertical supports holding two rear upright support members. Leg support members are rotatably mounted to the transverse support members. Coupled by ratchet devices to the rear of the seating means is a seat back. The seat back is composed of two vertical seat back members separated by horizontal seat back members. The ratchet allows the seat back to be 90 degrees from the seating means or to rearwardly pivot to parallel with said seating means. Legs formed at the top back of the seat back support the seat back against the ground when the seat back is fully reclined. Arm support members are pivotally coupled to the sides of seat back. Also disclosed are two pneumatic devices. The first pneumatically advances a horizontal armature. The second pneumatically advances a vertical armature.

5 Claims, 2 Drawing Sheets

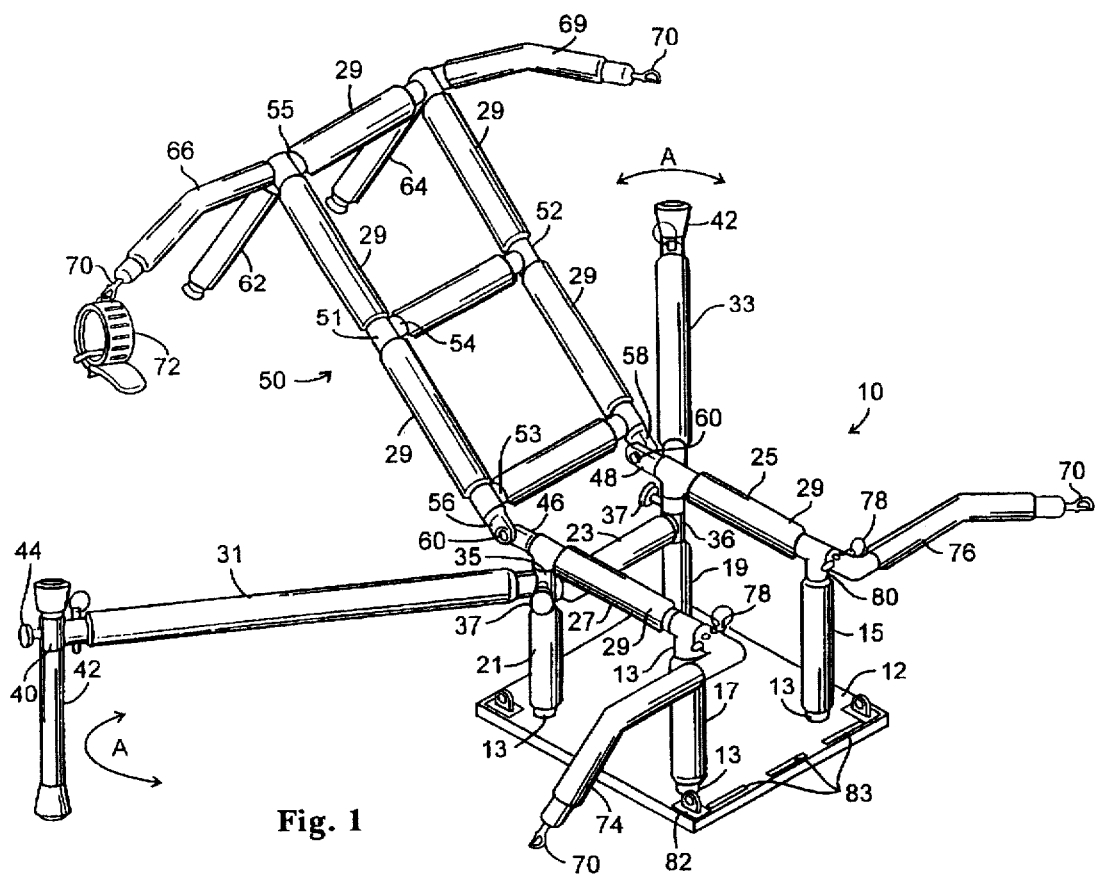
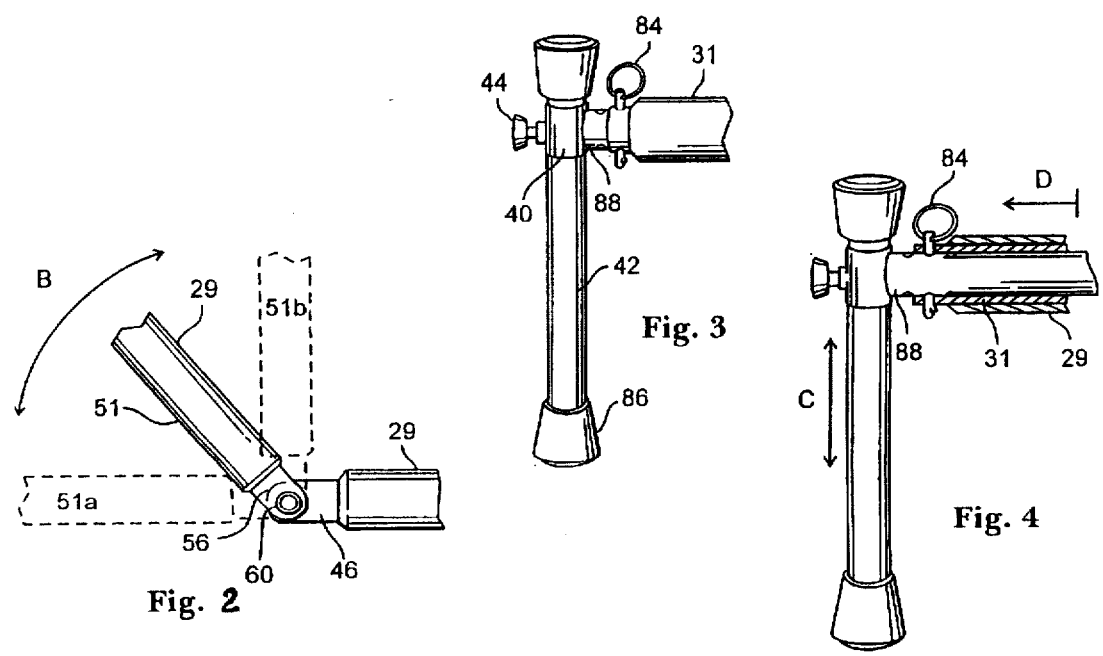

5,704,894

PNEUMATIC APPARATUS FOR CONTROLLING CERTAIN BODILY INSERTION DEVICES AND COLLAPSIBLE SEATING APPARATUS

This application is a division of application Ser. No. 08/368,907, filed 5 Jan. 1995, now U.S. Pat. No. 5,586,560.

BACKGROUND OF THE INVENTION

1. Field of the Invention

This invention relates to pneumatic apparatus with armature for controlling bodily insertion devices.

More particularly, the present invention relates to adjustable pneumatic apparatus and a collapsible seating apparatus which may used therewith.

In a further and more specific aspects, the invention relates to an adjustable, collapsible, and portable seating apparatus which can support the body in a variety of positions, including fully reclined.

2. Prior Art

Seating apparatus of many kinds are widely known. The art is replete with various apparatus used to sit upon, including adjustable chairs and folding chairs that store away in a minimum of space. Yet only medical appliances with a minimum of comfort, if any, are available for seating so that the sitter's legs are comfortably spread apart. Further very few seating apparatuses are available for restraining the sitter. Additionally, this seating apparatus has no specific seating surface.

Pneumatic devices of many kinds are widely known. Yet a pneumatic device comprising armature to which bodily insertion devices may be attached and then controlled to move forward via the pneumatics are believed to be unknown. Further unknown is such a device which may be adjustable on a vertical scale for proper alignment with bodily orifices.

It would be highly advantageous, therefore, to remedy the foregoing and other deficiencies inherent in the prior art.

Accordingly, it is an object of the present invention to provide improvements in seating apparatus.

Another object of the invention is the provision of improvements especially adapted for use in connection with seating apparatus allowing a myriad of seating and reclining positions.

And another object of the invention is to provide improved means for comfortable seating wherein the user's legs are spread apart in a comfortable fashion.

Still another object of the immediate invention is the provision of an improved pneumatic device used to move forward or advance bodily insertion devices.

Yet another object of the invention is to provide means for allowing the user to gently urge the armature of the pneumatic device to advance bodily insertion devices.

Yet still another object of the invention is the provision of improved means for adjusting the vertical position of the armature of the pneumatic device.

A further object of the instant invention is to provide improvements in seating apparatus which may used in connection with means for allowing the user to gently urge the armature of the pneumatic device to advance bodily insertion devices.

And a further object of the invention is the provision of a seating apparatus having a ratcheting back rest.

Yet a further object of this invention is to provide a seating apparatus having a ratcheting back rest that moves from upright to a fully reclining position.

And yet an object of the invention is the provision of a collapsible, easily portable seating apparatus having means for restraining the arms and legs of the sitter.

Still yet an object of the invention is the provision of a collapsible and portable seating apparatus.

And still yet an object of the invention is the provision of a comfortable seating apparatus with no seating surface.

SUMMARY OF THE INVENTION

Briefly, to achieve the desired objects of the instant invention in accordance with a preferred embodiment thereof, first provided is a seating apparatus having a base, front and rear upright support members, a brace between the rear upright support members, and two vertical members running from the front support to the rear support members. The two vertical members comprise the seating means. Extending from the rear upright support members are two vertical support braces terminating in sleeves to hold two rear upright support members.

Coupled by ratchet devices to the rear of the seating means is a seat back. The seat back is composed of two vertical seat back members separated by horizontal seat back members. The ratchet allows the seat back to be 90 degrees from the seating means or to rearwardly pivot to parallel with said seating means. Legs formed at the top back of the seat back support the seat back against the ground when the seat back is fully reclined.

Leg support members are coupled to the front of the seating means. The leg support members are coupled in such a way to allow them to pivot about, allowing the sitter to have its legs supported downwardly, level, or upwardly.

Arm support members are coupled to the sides of seat back. The arm support members are coupled in such a way to allow them to pivot about, allowing the sitter to have its arms supported downwardly, level, or upwardly. Clips for attaching restraining means are provided at the end of the leg and arm support members.

Also provided are two pneumatic armature devices. The first has a base, a vertical support member, and a horizontal pneumatic extension armature. The vertical support member has an outer sleeve connected to an air bulb with pressure release, and an inner extension member. The inner extension member terminates with a connector to which various bodily insertion devices may be attached.

The vertical support member is coupled to the horizontal member in such a way that allows the horizontal pneumatic extension armature to be lowered and raised along the vertical support member. The vertical support member also terminates in a large ball to provide the user a secure handle. Additionally wires can extended through the device to connect to electricity for electrode devices attached to the connector. The ball may also be electrified to become an electrode and a vibrator may be mounted within said ball.

Also provided is a vertical extension pneumatic device to which bodily insertion devices may be attached.

BRIEF DESCRIPTION OF THE DRAWINGS

The foregoing and further and more specific objects and advantages of the instant invention will become readily apparent to those skilled in the art from the following detailed description of a preferred embodiment thereof taken in conjunction with the drawings, in which:

FIG. 1 is a perspective view of the seating apparatus;

FIG. 2 is a partial view of the seating apparatus showing the ratcheting means between the seating means and the seat back, and its two extreme positions;

FIG. 3 is a partial view of the seating apparatus showing the rear vertical leg and part of the horizontal support member holding the leg.

FIG. 4 is a partial view of the seating apparatus showing the rear vertical leg and part of the horizontal support member holding the leg with the horizontal support member cut away to reveal its layers;

PREFERRED EMBODIMENT OF THE PRESENT INVENTION

Figure 5:
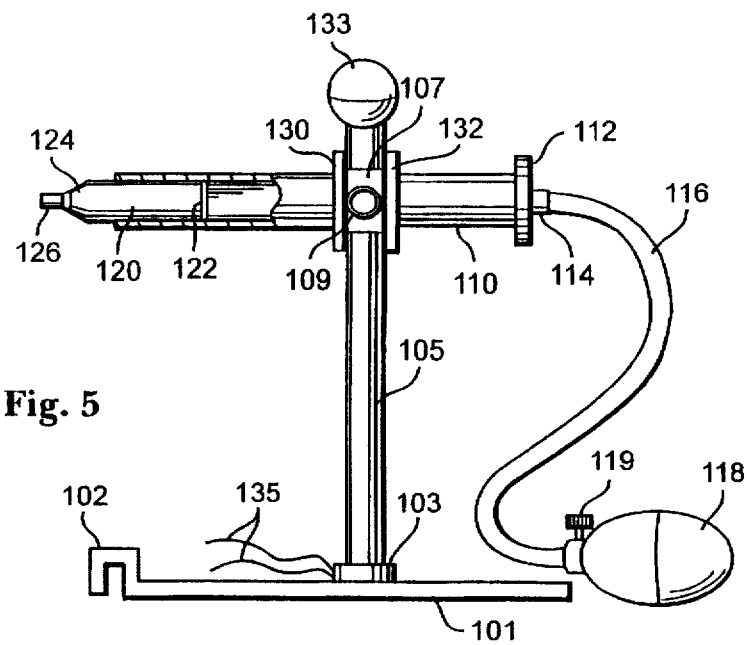
FIG. 5 is a side view of the adjustable horizontal pneumatic extension device.

Turning now to the drawings in which like reference characters indicate corresponding elements throughout the several views. Attention is first directed to FIG. 1 which shows seating apparatus 10. Seat 10 has base 12 to which tubular members 13 are attached. Front and rear upright support members 15, 17, 19, and 21 are tubular, and sleeve over tubular members 13.

Brace 23 is formed between rear upright support members 19 and 21.

Vertical members 25 and 27 run from front supports 15 and 17 to rear support members 19 and 21, respectively. Vertical members 25 and 27 comprise the seating means. A user's buttocks is supported on vertical members 25 and 27. Adding to comfort, vertical members 25 and 27 are coated with padded covering 29.

Extending from rear upright support members 21 and 19 are vertical support braces 31 and 33, respectively. Vertical support braces 31 and 33 are coupled to rear upright support members 21 and 19 via clamps 35 and 36. Each of clamps 35 and 36 has a butterfly screw 37 which fixes clamps 35 and 36 against rear upright support members 21 and 19. Releasing screw 37 allows the user to rotate vertical support braces 31 and 33 against rear upright support members 21 and 19 in an arc shown as arc A.

Vertical support braces 31 and 33 terminate in sleeves 40 which hold upright support members 42. Butterfly screws 44 holds supports 42 in place. This sleeved arrangement allows supports 42 to moved up or down along line C of FIG. 5, as will be described in more detail later.

Rear upright support members 19 and 21 terminate in a T with the front and rear of the T being tubular. The front of the T from member 21 is received within vertical member 25 and the front of the T from member 19 is received within vertical member 27.

Seat back 50 comprises vertical tubular members 51 and 52, with horizontal tubular members 53, 54, and 55 running between them. All such members are constructed from tubular pipes as are the rest of the pieces of the seating apparatus, and are coated with padding 29 as shown. Padding 29 provides substantial comfort to the one seated in seat 10.

Members 51 and 52 comprise at a first end, flattened sections, flats 56 and 58. Members 46 and 48 are short tubular pipes that have flats as shown. Holes bored in the flats of 46, 48, 56, 58, allow flat 56 to be pivotally connected to flat 46, and allow flat 58 to be pivotally connected to flat 48. The pivotal connection is made via ratchet 60. Members 46 and 48 sleevedly fit into the T of uprights 21 and 19 respectively.

At the top of seat back vertical members 51 and 52 are legs 62 and 64. Legs 62 and 64 support the seat back against the ground when the seat back is fully reclined.

Arm support members 66 and 68 are pivotally coupled to members 51 and 52, respectively. The pivotal coupling allows members 66 and 68 to pivot about, allowing the sitter to have its arms supported downwardly, level, or upwardly. At the ends of members 66 and 68 are release clasps 70. Clasps 70 permit the attaching of restraining devices like strap 72. Those skilled in the art will appreciate that restraining means could be rope, handcuffs, or any other restraining device.

Front upright support members 15 and 17 terminate in a T with the T also being tubular. Pivotally coupled to front of the T are leg support members 74 and 76. Since members 74 and 76 may pivot about, the sitter to have its legs supported downwardly, level, or upwardly. Pin 78 holds members 74 and 76 in position by fitting through the members and the respective T portions they sleeve onto, through holes 80, which are place around the leg support members so they can be held in a variety of positions. The desirable range of swing is from 45 degrees to 160 degrees.

All of seat 10 can disassemble into a series of padded pipes, padded pipe assemblies, straps, pins, butterfly screws, etc., by releasing the various connecting means an pulling the larger pipe diameter member from the sleeving engagement with the smaller diameter pipe member. For example pin 78 may be removed whereupon leg support members 74 and 76 may pulled off. Even members 46 and 48 may be released from their sleeves to release seat back 50 from the rest of seat 10.

Base 12 also has loops 82 which can be used to tie down seat 10, or can be used to attach a packing box where the disassembled parts of seat 10 are stored, and base 12 then becomes the top or side of the closed box.

Turning to FIG. 2, shown is the ratcheting swing of seat back 50, the direction of which is indicated by arrow B. When positioned so that back member 51 is at 51a, back 50 is fully reclined and legs 62 and 64 are against the ground supporting seat 10 in a bed like position. Back member 51 is at it maximum upright position at 51b. A stop in ratchet 60 prevents back 50 from moving any further, where the sitter's abdomen and back might be bent too far.

Turning to FIGS. 3 and 4 shown is the rear leg assembly that is at the end of supports 31 and 33. Leg 42 is supported within sleeve 40 and is secured within sleeve 40 by butterfly screw 44. Leg 42 has rubber foot 86 mounted at is top and bottom so can be turned around when either foot wears out. As shown in FIG. 3 sleeve 40 is mounted to inner pipe support 88 which fits within padded pipe 31. This arrangement allows leg 42 to extend out further when additional bracing of seat 10 is required. Pin 84 fits though holes in pipe 31 and a in inner pipe 88. Pipe 88 has a series of corresponding holes that allow leg 42 to be extended in the direction of D.

Setting up legs 42 can be the most important part of assembling seat 10 since they stabilize seat 10 and prevent it from falling backwards. After determining the best position along arc A, which is generally 40 and 120 degrees out, the user loosens screw 44 so that leg 42 is loose within sleeve 40. Then support 31 or 33 is lifted slowly just until base 12 begins to lift at the rear, and the leg is locked by tightening down screw 44.

Turning to FIG. 5 pneumatic apparatus 100 is shown. Apparatus 100 has base 101 with sleeve 103. Vertical pipe 105 fits at its bottom end within a hole in sleeve 103 sized accordingly to hold pipe 105. A horizontal sleeve member 107 is affixed to a vertical sleeve member (not shown).

Sleeve 107 rests about pipe 105. Screw 109 holds sleeve 107 in position along pipe 105, but sleeve 107 may be move up or down thereby raising the height of pipe 110 or lowering it so that the insertion device may be positioned at the right height.

Horizontal pipe 110 is mounted through the vertical sleeve member attached to horizontal sleeve member 107. Pipe 110 may be moved forward or back within the vertical sleeve member, and is held in place by a screw through the vertical sleeve member just like screw 109. Braces 130 and 132 are large disks mounted of the sleeve assembly and serve to stabilize the horizontal positioning of pipe 110.

Pipe 110 has seal 112, nipple 114, hose 116 which feeds into nipple 114, and pressure bulb 118 which is just like the bulb on a blood pressure tester, including a pressure relief valve 119.

Sleeved within pipe 110 is pipe 120 which has seal 122, narrowing end 124, and connector 126. Connector 126 is internally threaded so to engage various bodily insertion devices which terminate with a screw.

Vertical support member 105 also terminates in a large ball 133 to provide the user a secure handle to hold device 100 steady during setup and use. Additionally wires 135 can extended through apparatus 100 to connect electrode insertion devices attached to connector 126 to electricity. Ball 133 may also be electrified to become an electrode and a vibrator may be mounted within said ball.

Ideally the horizontal pneumatic apparatus shown herein is for use by females, with a vaginal plug. Seated for comfort on seat 10, or reclined in another seating apparatus, device 100 may be setup and positioned for proper height and distance therefrom. Then the user may gently squeeze bulb 118 slowly to gently advance the insertion device attached to connector 126, or may squeeze with more force and frequency to quickly and forcibly advance the insertion device. Note the vaginal plug could be a vaginal electrode.

Figure 6:
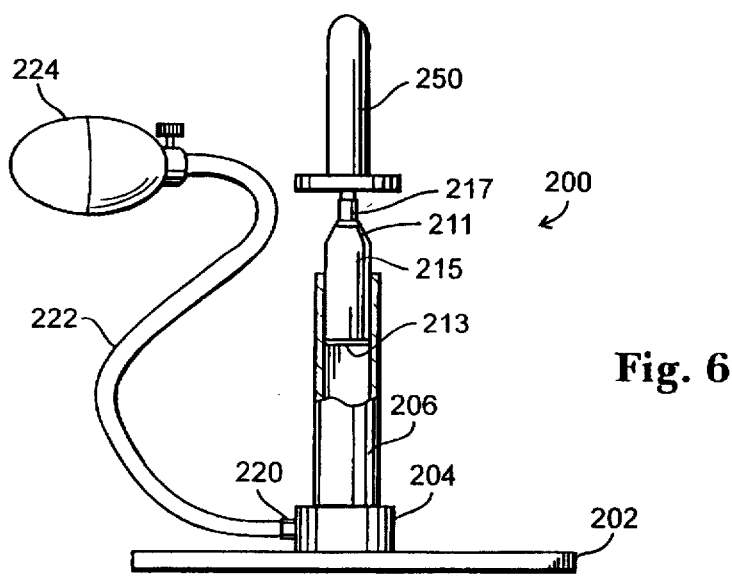
FIG. 6 is a side view of the vertical pneumatic extension device.

Also provided as shown in FIG. 6 is vertical extension pneumatic device 200 to which bodily insertion devices may be attached. Device 200 has base 202 with sleeve 204. Pipe 206 houses pipe 211. Nipple 220 is affixed to sleeve 204, and a hose 222 is attached. A pressure bulb 224, analogous to bulb 118 is affixed to the end of hose 222.

Pipe 211 has seal 213, narrowing section 215, and connector 217. Connector 217 has internal threads to which a screw mounted on the end of insertion device 250 connects.

Shown herein is an anal plug, which could be an electrode plug, too. Wires can be run through or along device 200 to connect an electrode insertion device to an electrical source.

Various changes and modifications to the embodiments herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. A pneumatic device comprising:

a base;

vertical pipe means rising from said base;

sleeve means disposed about said vertical pipe means and coupled to perpendicular sleeve means, said sleeve means being able to travel up and down along said vertical pipe means;

horizontal pipe means mounted in said perpendicular sleeve means, said horizontal pipe means being able to travel frontward and backward along said perpendicular sleeve means, and said horizontal pipe means housing an inner pipe;

said inner pipe having a seal at a first end, and a second end;

pressure bulb means coupled to hose means in air communication with said horizontal pipe means so that a squeeze of said bulb pushes air against said seal and moves said inner pipe within said horizontal pipe means.

2. The pneumatic device of claim 1 further comprising connecting means at the second end of said inner pipe.

3. The pneumatic device of claim 1 further comprising a metallic ball at the end of the vertical pipe means.

4. The pneumatic device of claim 3 further comprising wires to connect said ball to electricity.

5. The pneumatic device of claim 1 further comprising wires to connect to an electrode insertion device mounted on said connecting means.

\* \* \* \* \*